US011963857B2

(12) United States Patent
Furukawa

(10) Patent No.: US 11,963,857 B2
(45) Date of Patent: Apr. 23, 2024

(54) ABSORBENT ARTICLE

(71) Applicant: Daio Paper Corporation, Ehime (JP)

(72) Inventor: Masashi Furukawa, Ehime (JP)

(73) Assignee: Daio Paper Corporation, Ehime (JP)

( * ) Notice: Subject to any disclaimer, the term of this patent is extended or adjusted under 35 U.S.C. 154(b) by 841 days.

(21) Appl. No.: 16/979,569

(22) PCT Filed: Mar. 19, 2019

(86) PCT No.: PCT/JP2019/011378
§ 371 (c)(1),
(2) Date: Sep. 10, 2020

(87) PCT Pub. No.: WO2019/188566
PCT Pub. Date: Oct. 3, 2019

(65) Prior Publication Data
US 2021/0007910 A1    Jan. 14, 2021

(30) Foreign Application Priority Data
Mar. 29, 2018 (JP) .................. 2018-065934

(51) Int. Cl.
| A61F 13/514 | (2006.01) |
| A61F 5/441  | (2006.01) |
| A61F 13/51  | (2006.01) |
| A61F 13/539 | (2006.01) |
| A61F 13/551 | (2006.01) |
| D21H 11/18  | (2006.01) |
(Continued)

(52) U.S. Cl.
CPC ........ *A61F 13/51401* (2013.01); *A61F 5/441* (2013.01); *A61F 13/551* (2013.01);
(Continued)

(58) Field of Classification Search
CPC ...... A61F 13/49; A61F 13/8405; A61F 13/51; A61F 2013/51002; A61F 2013/21019;
(Continued)

(56) References Cited

U.S. PATENT DOCUMENTS

2005/0033257 A1*  2/2005  Miyoshi ............ A61F 13/51478
                                                      604/389
2005/0131366 A1*  6/2005  Shimada ........... A61F 13/51478
                                                      428/137
(Continued)

FOREIGN PATENT DOCUMENTS

JP    2000-350745    12/2000
JP    2001-046423     2/2001
(Continued)

OTHER PUBLICATIONS

International Search Report for PCT/JP2019/011378, dated May 14, 2019.
(Continued)

*Primary Examiner* — Benjamin J Klein
*Assistant Examiner* — Meagan Ngo
(74) *Attorney, Agent, or Firm* — Andrus Intellectual Property Law, LLP

(57) ABSTRACT

An absorbent article that improves contact efficiency between a deodorant substance and an odor. The problem is solved by an absorbent article including an absorber and a liquid impervious resin film covering an outside of the absorber, in which a cellulose nanofiber layer is attached directly to a member outside the liquid impervious resin film, and the cellulose nanofiber layer can come into contact with an odor in an atmosphere outside the absorbent article.

11 Claims, 12 Drawing Sheets

(51) Int. Cl.
*B82Y 30/00* (2011.01)
*B82Y 40/00* (2011.01)

(52) U.S. Cl.
CPC .... *D21H 11/18* (2013.01); *A61F 2013/51019* (2013.01); *A61F 2013/5109* (2013.01); *A61F 2013/53908* (2013.01); *B82Y 30/00* (2013.01); *B82Y 40/00* (2013.01)

(58) Field of Classification Search
CPC .... A61F 2013/5109; A61F 2013/51452; A61F 13/51478; A61F 2013/51441; A61F 13/514; A61F 13/51462; A61F 5/441; A61F 2013/8408
See application file for complete search history.

(56) References Cited

U.S. PATENT DOCUMENTS

| | | | |
|---|---|---|---|
| 2008/0160856 A1* | 7/2008 | Chen | D04H 1/43838 442/341 |
| 2011/0172507 A1* | 7/2011 | Lademann | A61L 15/56 604/372 |
| 2017/0135869 A1* | 5/2017 | Moriya | A61F 13/51108 |
| 2019/0000676 A1* | 1/2019 | Shirai | A61F 13/0256 |
| 2019/0321240 A1* | 10/2019 | Sakaguchi | A61F 13/15 |

FOREIGN PATENT DOCUMENTS

| | | |
|---|---|---|
| JP | 4236117 | 3/2009 |
| JP | 2010-154928 | 7/2010 |
| JP | 4652387 | 3/2011 |
| WO | 2008/065748 | 6/2008 |
| WO | 2017014255 | 1/2017 |

OTHER PUBLICATIONS

"Development Process of China's Chemical Fiber Industry Technology" pp. 233-234.

* cited by examiner

[FIG. 1]
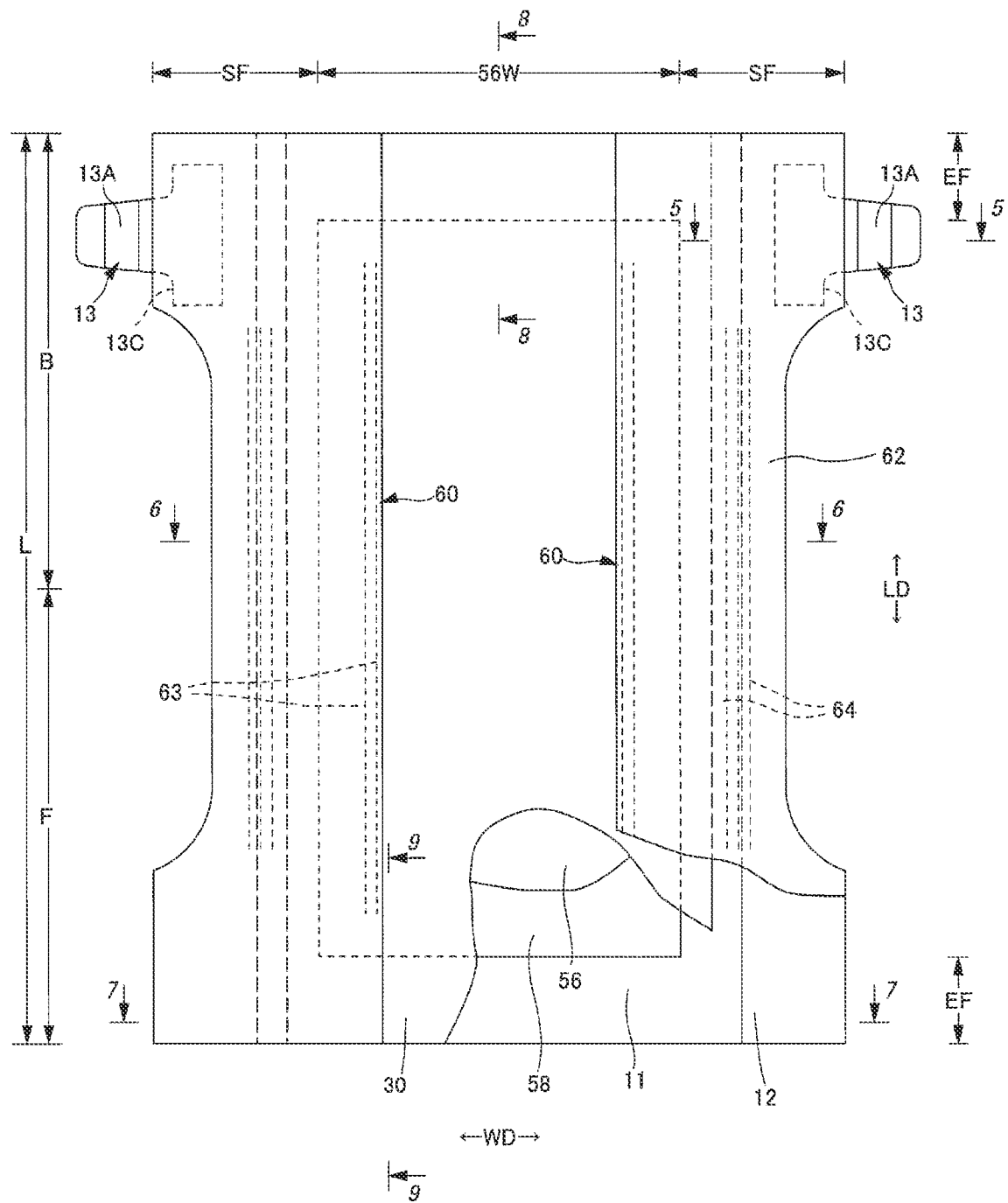

[FIG. 2]
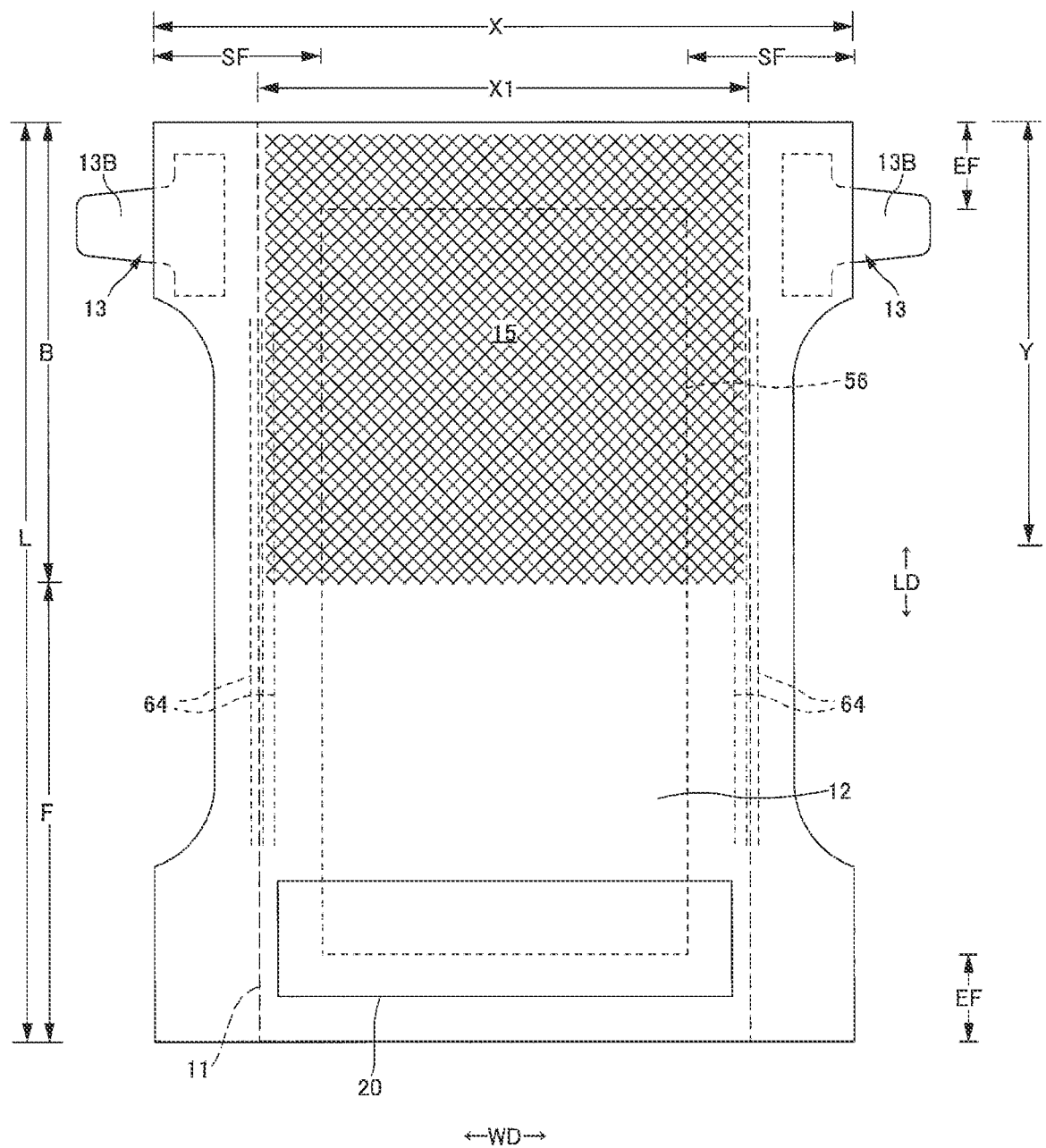

[FIG. 3]
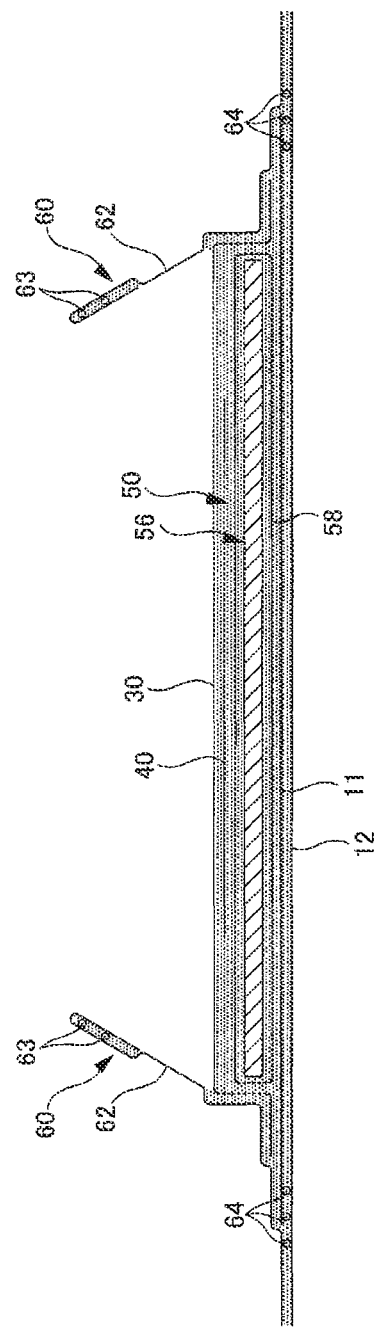

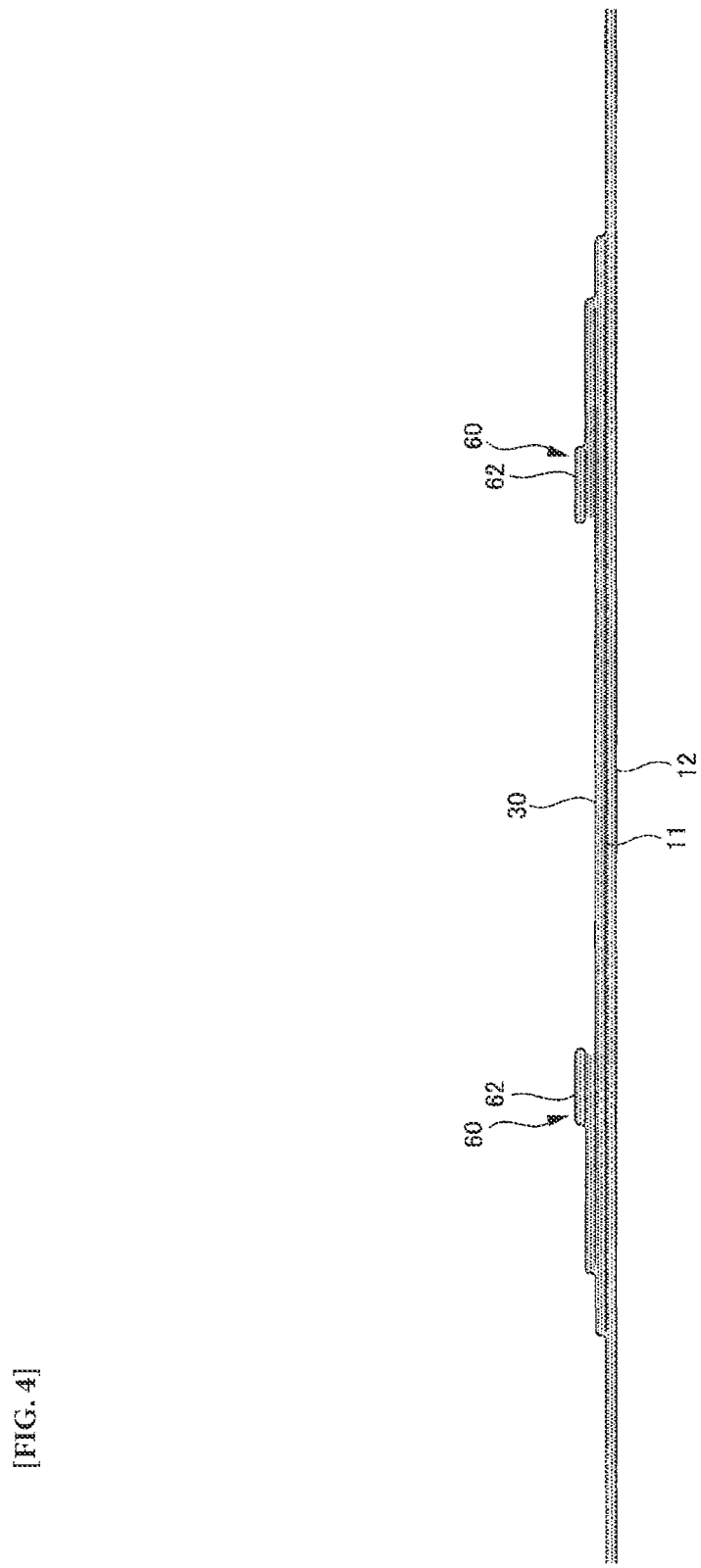

[FIG. 5]
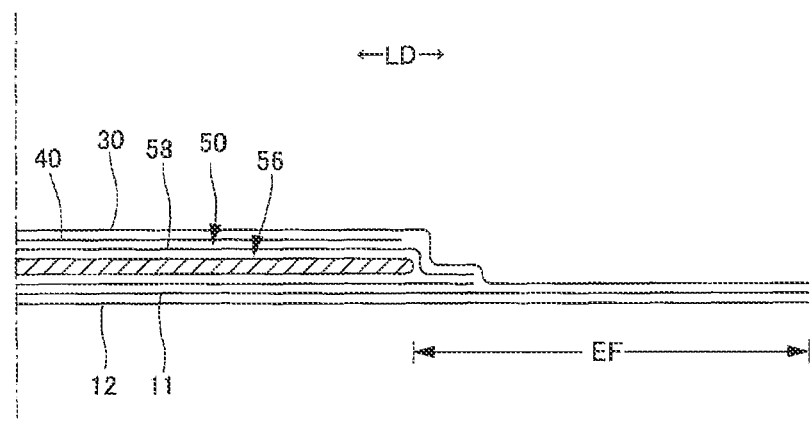

[FIG. 6]
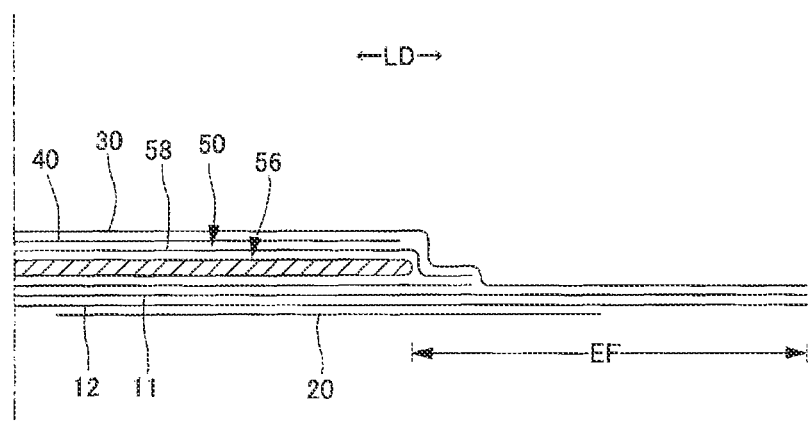

[FIG. 7]
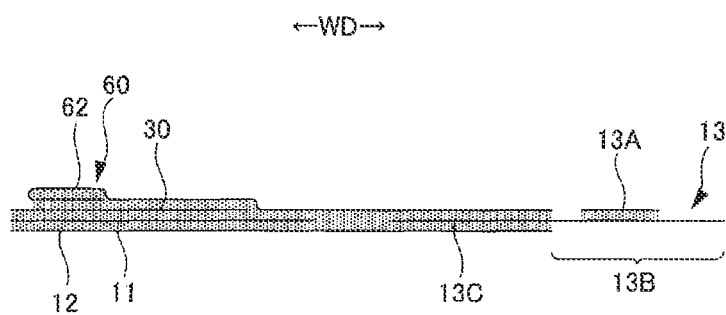

[FIG. 8]
(a)
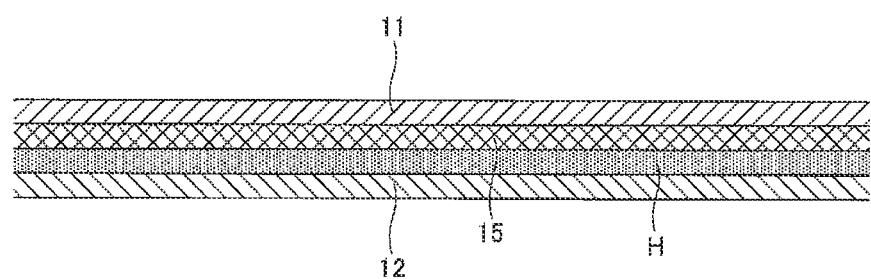
(b)
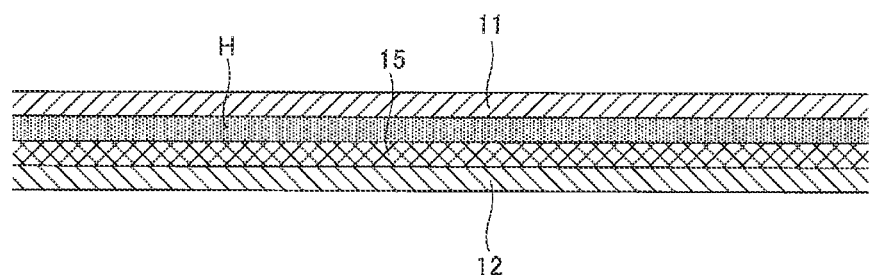

[FIG. 9]
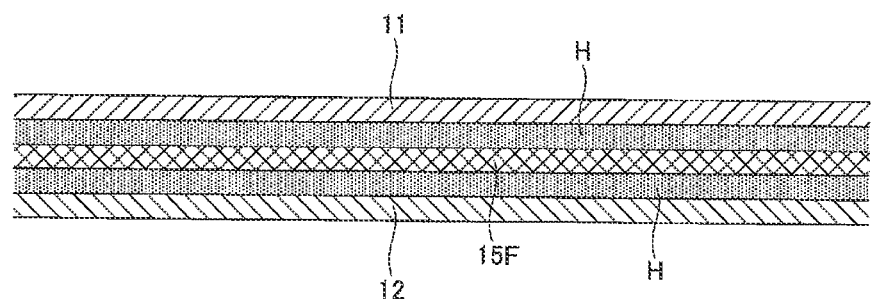

[FIG. 10]
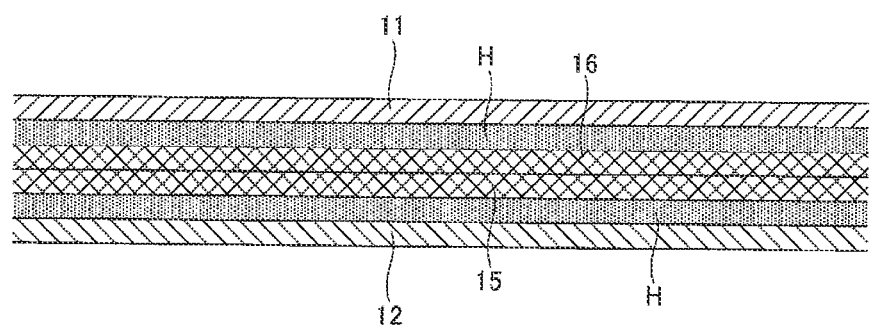

[FIG. 11]
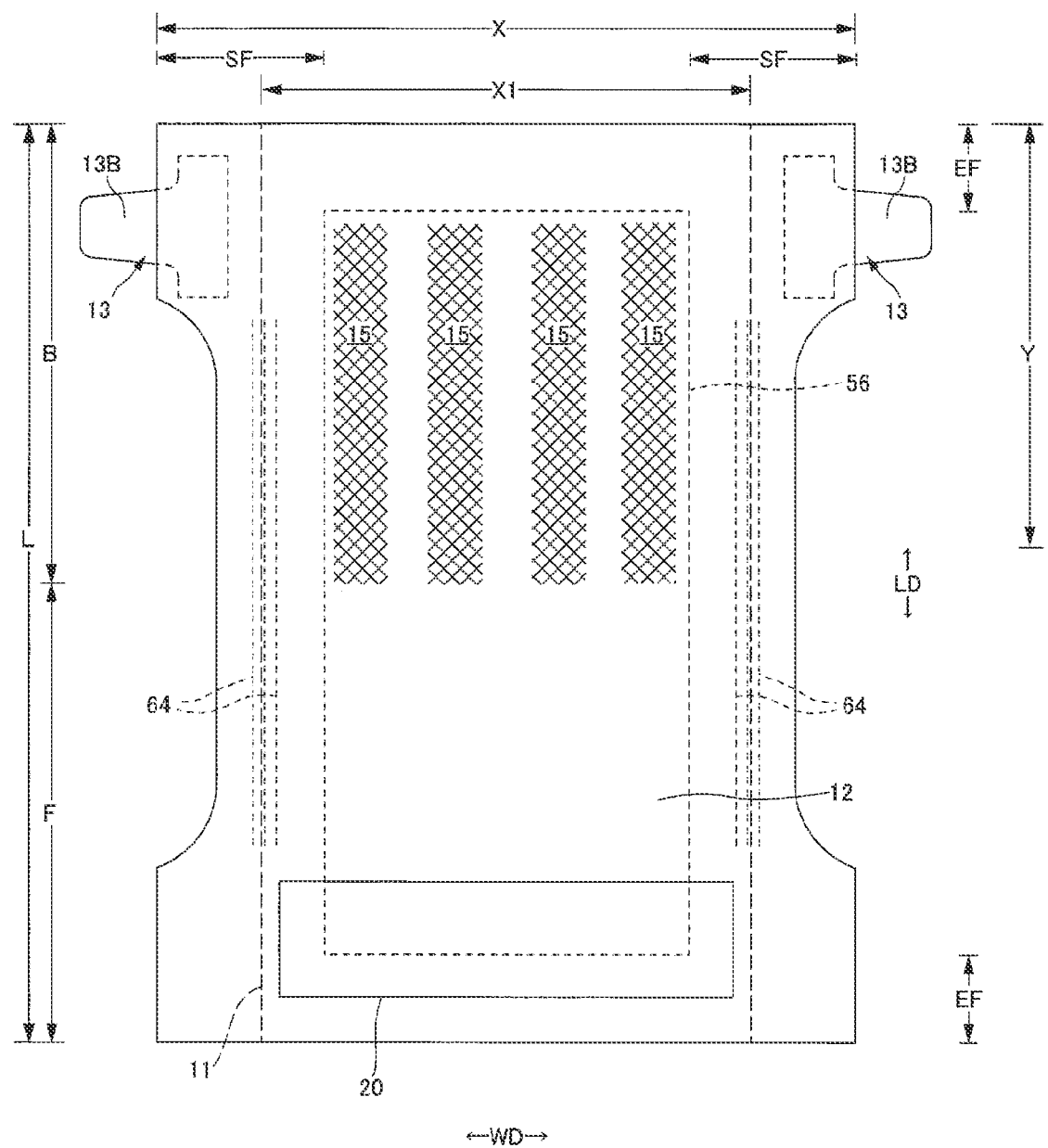

[FIG. 12]
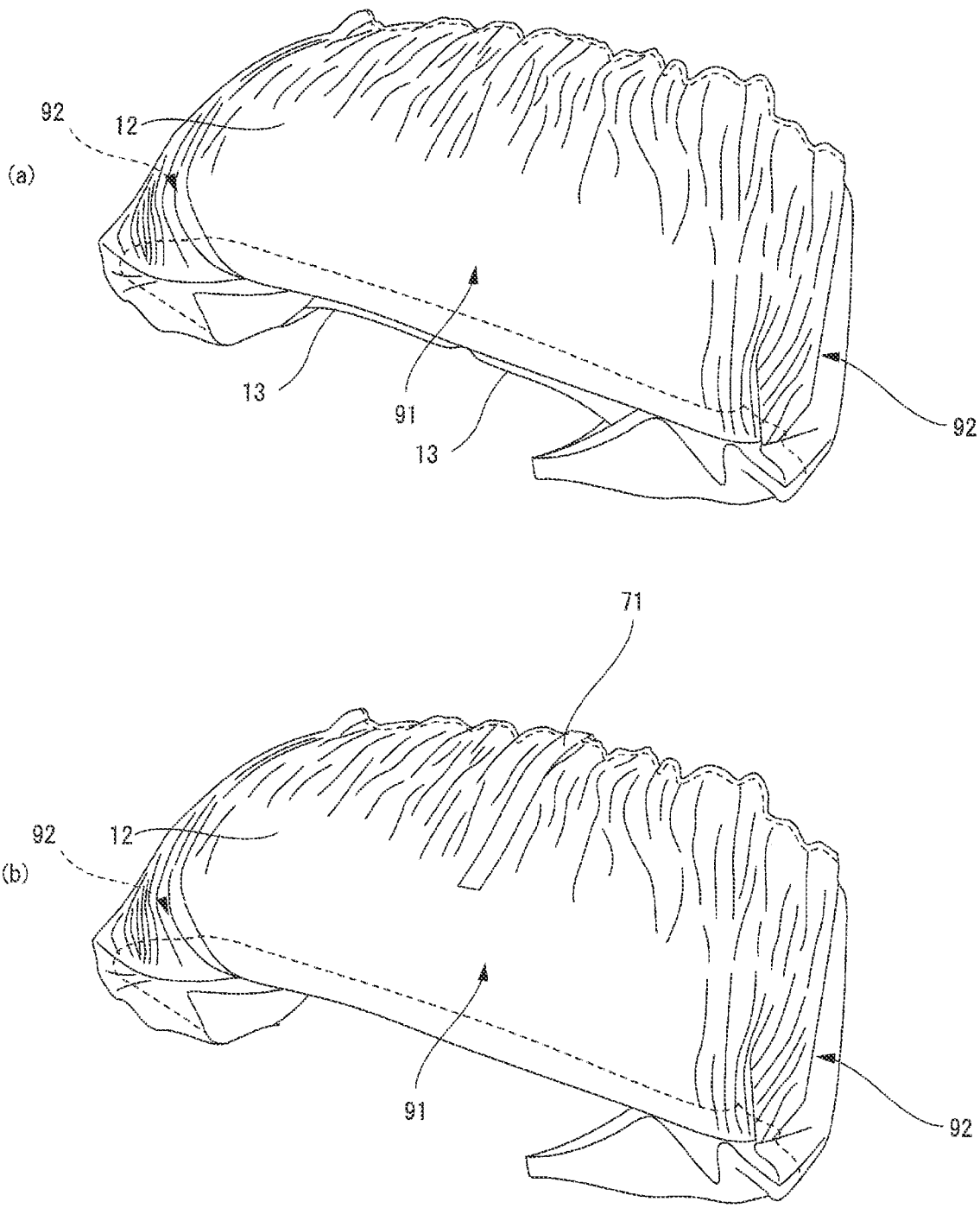

ABSORBENT ARTICLE

CROSS-REFERENCE TO RELATED APPLICATIONS

This application is the U.S. national stage application of International Application PCT/JP2019/011378, filed Mar. 19, 2019, which international application was published on Oct. 3, 2019, as International Publication WO 2019/188566 in the Japanese language. The International Application claims priority of Japanese Patent Application No. 2018-065934, filed Mar. 29, 2018. The international application and Japanese application are both incorporated herein by reference, in entirety.

TECHNICAL FIELD

The present invention relates to an absorbent article such as a disposable diaper including an underpants-type diaper and a tape-type diaper, or a sanitary napkin.

BACKGROUND ART

Generally, an absorbent article such as a disposable diaper or a sanitary napkin is used in such a form that the absorbent article is rolled or folded such that an excrement adherence surface is an internal side after use, put in a highly airtight storage container such as a sanitary box or a diaper storage container for temporary storage, and put in a garbage bag and discarded when the amount thereof stored in the container reaches a certain level. A strong odor of excrement is generated from an absorbent article after use, causing discomfort to a user. Therefore, in order to suppress an odor of excrement after use, disposition of a deodorant sheet containing zeolite inside a top sheet (Patent Literature 1), inclusion of a deodorant in crepe paper wrapping an absorber (Patent Literature 2), and the like have been proposed.

CITATION LIST

Patent Literature

Patent Literature 1: JP 2001-046423 A
Patent Literature 2: JP 2000-350745 A
Patent Literature 3: JP 4236117 B2
Patent Literature 4: JP 4652387 B2

SUMMARY OF INVENTION

Technical Problem

However, since a general solid deodorant substance does not have adhesiveness by itself, it is necessary to use a fixing means such as a hot melt adhesive or a pressure-sensitive adhesive in order to securely fix the deodorant substance to an absorbent article. In this case, there is not only a disadvantage that cost of the fixing means increases but also a disadvantage that a part or all of deodorant particles are covered with the fixing means to reduce contact efficiency of the deodorant particles with an odor.

Therefore, a main object of the present invention is to improve contact efficiency between a deodorant substance and an odor.

Solution to Problem

Various aspects of an absorbent article that has solved the above problem are as follows.

<Invention Recited in Claim 1>
An absorbent article including:
an absorber; and
a liquid impervious resin film covering an outside of the absorber, wherein
a cellulose nanofiber layer is attached directly to a member outside the liquid impervious resin film, and
the cellulose nanofiber layer can come into contact with an odor in an atmosphere outside the absorbent article.
(Action and Effect)
The present inventor made intensive studies in order to solve the above problem, and has found that the cellulose nanofiber layer has sufficient adhesiveness by itself, and has an effect of physically adsorbing an odor to reduce the odor. The present invention is based on this finding. According to the present invention, the cellulose nanofiber layer is attached directly to a member outside the liquid impervious resin film (this means that the cellulose nanofiber layer is attached to the member only by adhesiveness of the cellulose nanofibers without using an adhesive or the like, the same hereinafter), and the cellulose nanofiber layer can come into contact with an odor in an atmosphere outside the absorbent article. Therefore, the cellulose nanofiber layer has high contact efficiency with an odor, and an odor outside the absorbent article, particularly an odor inside a storage container when the absorbent article is temporarily stored in the storage container can be reduced more effectively. Note that Patent Literatures 3 and 4 each describe an invention of applying cellulose nanofibers to an absorbent article, but are not intended to reduce an odor.

<Invention Recited in Claim 2>
The absorbent article according to claim 1, including an exterior nonwoven fabric covering an external surface of the liquid impervious resin film, wherein
the cellulose nanofiber layer is interposed between the liquid impervious resin film and the exterior nonwoven fabric, and
the exterior nonwoven fabric has a fiber fineness of 1.0 to 6.0 dtex, a fiber basis weight of 15 to 45 g/m², and a thickness of 0.5 to 3.0 mm.
(Action and Effect)
A portion having the cellulose nanofiber layer is inevitably hard, and an external surface of the absorbent article may have a hard texture. Therefore, as described above, it is preferable to make transmission of the hardness of the cellulose nanofiber layer difficult to suppress deterioration of the texture of the external surface of the absorbent article by covering the cellulose nanofiber layer with a relatively thick and firm exterior nonwoven fabric.

<Invention Recited in Claim 3>
The absorbent article according to claim 1 or 2, including:
a ventral side portion located on a front side of a center in a front-back direction and a dorsal side portion located on a back side of the center in the front-back direction; and
a tape for disposal protruding from both side portions of the dorsal side portion or protruding from a width direction intermediate portion of the dorsal side portion, wherein
the cellulose nanofiber layer is disposed in the dorsal side portion, and the cellulose nanofiber layer is not disposed in the ventral side portion.
(Action and Effect)
As an absorbent article, a form is widely adopted in which a tape for disposal is fixed to an external surface of an absorbent article in a state of being rolled or folded such that an internal surface of the absorbent article is an internal side at the time of discard. In such a state of discard, as illustrated in FIG. 12, an external surface of the absorbent article is covered with the dorsal side portion, and an odor generated from excrement adhering to an internal surface of the absorbent article or excrement absorbed by the absorber is released to the outside through the dorsal side portion of the external surface. Therefore, when a cellulose nanofiber layer is disposed in the dorsal side portion, the cellulose nanofiber layer is located in a main path of an odor in a discard form in which the absorbent article is rolled or folded, and therefore an odor reducing effect is exhibited more effectively. Furthermore, in a discard form in which the absorbent article is rolled or folded, the cellulose nanofiber layer is located closer to the external surface. Therefore, an odor reducing effect is exhibited also to an odor existing outside the article, such as an odor in a storage container. In addition, with such a configuration, an odor reducing effect is exhibited effectively without disposing the cellulose nanofiber layer on the entire site outside the liquid impervious resin film, and therefore cost effectiveness is also excellent.

<Invention Recited in Claim 4>

The absorbent article according to any one of claims 1 to 3, wherein
  the cellulose nanofiber layer is disposed only in a range where the cellulose nanofiber layer overlaps with the absorber.

(Action and Effect)

A portion having the cellulose nanofiber layer is inevitably hard. On a skin side of a wearer, the hardness of the cellulose nanofiber layer is hidden by a cushioning property of the absorber in a region where the cellulose nanofiber layer overlaps with the absorber. However, in a portion having no absorber, it cannot be expected that the hardness will be hidden by the absorber. Therefore, it is desirable to dispose the cellulose nanofiber layer only in a range where the cellulose nanofiber layer overlaps with the absorber.

<Invention Recited in Claim 5>

The absorbent article according to any one of claims 1 to 4, including an exterior nonwoven fabric covering an external surface of the liquid impervious resin film, wherein
  the cellulose nanofiber layers are disposed between the liquid impervious resin film and the exterior nonwoven fabric at a plurality of positions at intervals in at least one of a front-back direction and a width direction, and are attached directly to at least the liquid impervious resin film,
  the liquid impervious resin film is bonded to the exterior nonwoven fabric at a portion not having the cellulose nanofiber layers via a hot melt adhesive, and
  a part or the whole of each of the cellulose nanofiber layers is not covered with the hot melt adhesive.

(Action and Effect)

Considering adhesiveness of the cellulose nanofiber layer, contact efficiency thereof with an external odor, and texture of an external surface, it is preferable to attach the cellulose nanofiber layer to an external surface of the liquid impervious resin film, and to cover an outside thereof with the exterior nonwoven fabric. Here, the exterior nonwoven fabric is usually bonded to the liquid impervious resin film via a hot melt adhesive. However, covering the cellulose nanofiber layer with the hot melt adhesive is not desirable for improving contact efficiency between the cellulose nanofiber layer and an odor. In contrast, as described above, when a structure is formed in which the cellulose nanofiber layers are disposed at a plurality of positions at intervals, the liquid impervious resin film is bonded to the exterior nonwoven fabric at this interval portion, and a part or the whole of each of the cellulose nanofiber layers is not covered with a hot melt adhesive, it is possible to suppress a decrease in contact efficiency between each of the cellulose nanofiber layers and an odor while the exterior nonwoven fabric is bonded to the liquid impervious resin film, which is preferable.

In addition, the cellulose nanofiber layer is hard. Therefore, when the cellulose nanofiber layer is disposed continuously in a broad range, softness of a product may be impaired. In contrast, when the cellulose nanofiber layers are disposed at intervals, it is possible to suppress a decrease in softness while the cellulose nanofiber layers are disposed in a broad range. Meanwhile, cellulose nanofibers absorb an odor by physical adsorption. The cellulose nanofibers are fibrous, and therefore have a high aspect ratio and a relatively large specific surface area. Therefore, the cellulose nanofibers have a better physical adsorption property than general deodorant particles, and therefore have a large odor reducing effect even if the cellulose nanofiber layers are disposed at intervals. In addition, the use amount of the cellulose nanofibers can be reduced, and therefore cost effectiveness is also excellent.

<Invention Recited in Claim 6>

The absorbent article according to any one of claims 1 to 5, wherein
  the cellulose nanofibers of the cellulose nanofiber layer have an average fiber width of 10 to 100 nm, and
  the cellulose nanofiber layer includes 0.1 to 5.0 $g/m^2$ cellulose nanofibers.

(Action and Effect)

The average fiber width of the cellulose nanofibers and the use amount thereof are not particularly limited, but are preferably within the above ranges in a usual case.

Advantageous Effects of Invention

The present invention provides an absorbent article having improved contact efficiency between a deodorant substance and an odor.

BRIEF DESCRIPTION OF DRAWINGS

FIG. 1 is a plan view illustrating an internal surface of a tape-type disposable diaper in a state where the diaper is unfolded.

FIG. 2 is a plan view illustrating an external surface of a tape-type disposable diaper in a state where the diaper is unfolded, and illustrating an application portion of a cellulose nanofiber layer.

FIG. 3 is a cross-sectional view cut along 6-6 of FIG. 1.
FIG. 4 is a cross-sectional view cut along 7-7 of FIG. 1.
FIG. 5 is a cross-sectional view cut along 8-8 of FIG. 1.
FIG. 6 is a cross-sectional view cut along 9-9 of FIG. 1.
FIG. 7 is a cross-sectional view cut along 5-5 of FIG. 1.
FIG. 8 is a cross-sectional view illustrating a main part.
FIG. 9 is a cross-sectional view illustrating a main part.
FIG. 10 is a cross-sectional view illustrating a main part.
FIG. 11 is a plan view illustrating an external surface of a tape-type disposable diaper in a state where the diaper is unfolded, and illustrating an application portion of a cellulose nanofiber layer.
FIG. 12 is an explanatory diagram of a state where a disposable diaper is discarded.

DESCRIPTION OF EMBODIMENTS

After excretion by a wearer, a tape-type diaper is wrapped such that excrement cannot be seen from the outside and discarded. As an example of how to discard a tape-type diaper, the diaper is wound in a dorsoventral direction such that an internal surface of the diaper is an internal side to form a substantially cylindrical form (discard form) (see FIG. 12(a)). In this way, even if excrement is wrapped in a substantially cylindrical form, an odor of excrement is diffused out of the substantially cylindrical form. Therefore, a diaper with improved contact efficiency between a deodorant substance and an odor is proposed below.

FIGS. 1 to 7 illustrate an example of a tape-type disposable diaper. A reference character X in the drawings represents the maximum width of the diaper excluding a connecting tape. A reference character L represents the maximum length of the diaper. A dotted pattern portion in the cross-sectional views illustrates an adhesive as a bonding means for bonding constituent members located on an internal surface side and an external surface. The constituent members are formed by applying a hot melt adhesive by solid application, bead application, curtain application, summit application, spiral application, pattern coating (transfer of a hot melt adhesive by a letterpress method), or the like. Alternatively, a fixing portion of an elastic member is formed, instead of this or in addition to this, by application to an outer peripheral surface of an elastic member by a comb gun, SureWrap application, or the like. Examples of the hot melt adhesive include an EVA-based agent, a pressure-sensitive rubber-based agent (elastomer-based agent), a polyolefin-based agent, and a polyester/polyamide-based agent, and these can be used without particular limitation. As a bonding means for bonding constituent members, a means by material welding such as heat sealing or ultrasonic sealing can also be used.

This tape-type disposable diaper includes an absorber 56, a liquid pervious top sheet 30 covering an internal surface of the absorber 56, a liquid impervious resin film 11 covering an external surface of the absorber 56, and an exterior nonwoven fabric 12 covering an external surface of the liquid impervious resin film and forming a product external surface. A reference character F represents a ventral side portion located in a front side of a center in a front-back direction. A reference character B represents a dorsal side portion located in a dorsal side of the center in the front-back direction.

Hereinafter, a material of each portion and a characteristic part thereof will be described sequentially.

(Absorber)

The absorber 56 absorbs and holds an excrement liquid, and can be formed by an assembly of fibers. As this fiber assembly, in addition to those obtained by accumulating short fibers such as fluff pulps or synthetic fibers, a filament assembly obtained by opening a tow (fiber bundle) of synthetic fibers such as cellulose acetate as necessary can also be used. In a case where fluff pulps or short fibers are accumulated, a fiber basis weight may be, for example, about 100 to 300 g/m². In a case of a filament assembly, a fiber basis weight may be, for example, about 30 to 120 g/m². In a case of a synthetic fiber, a fineness is, for example, 1 to 16 dtex, preferably 1 to 10 dtex, and more preferably 1 to 5 dtex. In a case of a filament assembly, the filament may be formed of non-crimped fibers but is preferably formed of crimped fibers. The degree of crimp of the crimped fibers may be, for example, about 5 to 75, preferably 10 to 50, and more preferably 15 to 50 per 2.54 cm. In addition, a uniformly crimped fiber can be used.

(Super Absorbent Polymer Particles)

The absorber 56 may contain super absorbent polymer particles partially or entirely. The super absorbent polymer particles include "powder" in addition to "particles". As super absorbent polymer particles 54, those used for this type of absorbent article can be used as they are. The particle diameters of the super absorbent polymer particles are not particularly limited. However, for example, when sieving using a standard sieve of 500 μm (JIS Z8801-1: 2006) (shake for five minutes) is performed, and particles falling under the sieve using this sieving are sieved using a standard sieve of 180 μm (JIS Z8801-1: 2006) (shake for five minutes), it is desirable that a ratio of particles remaining on the standard sieve of 500 μm is 30% by weight or less, and a ratio of particles remaining on the standard sieve of 180 μm is 60% by weight or more.

A material of the super absorbent polymer particles can be used without particular limitation, but those having a water absorption capacity of 30 g/g or more are preferable. Examples of the super absorbent polymer particles include a starch-based material, a cellulose-based material, and a synthetic polymer-based material. A starch-acrylic acid (salt) graft copolymer, a saponified product of a starch-acrylonitrile copolymer, a cross-linked product of sodium carboxymethyl cellulose, an acrylic acid (salt) polymer, or the like can be used. As the shapes of the super absorbent polymer particles, a usually used particulate material shape is suitable, but other shapes can also be used.

As the super absorbent polymer particles, those having a water absorption rate of 70 seconds or less, particularly 40 seconds or less are suitably used. When the water absorption rate is too slow, so-called returning that a liquid supplied into the absorber 56 returns out of the absorber 56 tends to occur.

As the super absorbent polymer particles, those having a gel strength of 1000 Pa or more are suitably used. This makes it possible to effectively suppress sticky feeling after liquid absorption even in a case of using the bulky absorber 56.

The basis weight of the super absorbent polymer particles can be appropriately determined depending on the absorption amount required for an application of the absorber 56. Therefore, the basis weight can be 50 to 350 g/m² although this cannot be applied generally. The basis weight of a polymer of less than 50 g/m² makes it difficult to secure the absorption amount. When the basis weight exceeds 350 g/m², not only the effect is saturated but also the excess of the super absorbent polymer particles imparts a gritty and uncomfortable feel.

(Wrapping Sheet)

The absorber 56 can be incorporated as an absorbent element 50 wrapped in a wrapping sheet 58 in order to prevent escape of the super absorbent polymer particles or to improve shape maintenance of the absorber 56. As the wrapping sheet 58, tissue paper, particularly crepe paper, a nonwoven fabric, a polylaminated nonwoven fabric, a sheet with small holes, and the like can be used. However, it is desirable that the wrapping sheet 58 is a sheet from which super absorbent polymer particles do not escape. When a nonwoven fabric is used instead of crepe paper, a hydrophilic spunbonded/melt blown/melt blown/spunbonded (SMMS) nonwoven fabric is particularly suitable, and polypropylene, polyethylene/polypropylene, or the like can be used as a material thereof. A nonwoven fabric having a fiber basis weight of 5 to 40 g/m², particularly of 10 to 30 g/m² is desirable.

As illustrated in FIG. 3, the single wrapping sheet 58 may wrap the whole of the absorber 56, or a plurality of the wrapping sheets 58 such as upper and lower two wrapping sheets 58 may wrap the whole of the absorber 56. The wrapping sheet 58 can also be omitted.

(Top Sheet)

As the top sheet 30, a liquid pervious sheet, for example, a perforated or imperforated nonwoven fabric or a porous plastic sheet can be used. Among these materials, the nonwoven fabric is not particularly limited concerning a raw material fiber thereof. Examples thereof include a synthetic fiber such as a polyolefin-based fiber including polyethylene and polypropylene, a polyester-based fiber, or a polyamide-based fiber, a regenerated fiber such as rayon or cupra, a natural fiber such as cotton, and a mixed fiber and a composite fiber in which two or more kinds of these fibers are used. Furthermore, the nonwoven fabric may be manufactured by any processing. Examples of a processing method include known methods such as a spunlacing method, a spunbonding method, a thermal bond method, a melt blown method, a needle punching method, an air through method, and a point bond method. For example, if softness and drapeability are demanded, a spunlacing method is a preferable processing method. If bulkiness and softness are demanded, a thermal bond method is a preferable processing method.

The top sheet 30 extends from a front end to a back end of the product in the front-back direction and extends to a lateral side more than the absorber 56 in the width direction WD. For example, when a starting point of a rising gather 60 described later is located closer to the center in the width direction than a side edge of the absorber 56, appropriate deformation can be made, for example, the width of the top sheet 30 is made shorter than the maximum width of the absorber 56 as necessary.

(Intermediate Sheet)

In order to quickly transfer a liquid that has passed through the top sheet 30 to the absorber, it is possible to dispose an intermediate sheet (also referred to as "second sheet") 40 having a higher liquid transmission rate than the top sheet 30. The intermediate sheet 40 is used in order to rapidly transfer a liquid to the absorber to enhance absorption performance of the absorber, and to prevent a "returning" phenomenon of the absorbed liquid from the absorber. The intermediate sheet 40 can be omitted.

Examples of the intermediate sheet 40 include a similar material to that of the top sheet 30, a spunlaced nonwoven fabric, a spunbonded nonwoven fabric, an SMS nonwoven fabric, a pulp nonwoven fabric, a mixed sheet of pulp and rayon, a point bonded nonwoven fabric, and crepe paper. In particular, an air through nonwoven fabric is preferable because of being bulky. As the air through nonwoven fabric, a composite fiber having a core-sheath structure is preferably used. In this case, a resin used for the core may be polypropylene (PP) but is preferably polyester (PET) having high rigidity. The basis weight is preferably 17 to 80 g/m$^2$, and more preferably 25 to 60 g/m$^2$. A raw material fiber of the nonwoven fabric preferably has a fineness of 2.0 to 10 dtex. In order to make the nonwoven fabric bulky, as mixed fibers of all or some of raw material fibers, eccentric fibers having no core in the center, hollow fibers, eccentric and hollow fibers are also preferably used.

The intermediate sheet 40 in the illustrated example is disposed at the center so as to be shorter than the width of the absorber 56, but may be disposed over the maximum width. The intermediate sheet 40 may be disposed over the maximum length of the diaper, but may be disposed only in an intermediate portion including an excrement position as in the illustrated example.

(Liquid Impervious Resin Film)

The liquid impervious resin film 11 is not particularly limited as long as having moisture perviousness. However, for example, a microporous sheet obtained by kneading an inorganic filler in a polyolefin-based resin such as polyethylene or polypropylene, molding a sheet, and then stretching the sheet in a monoaxial or biaxial direction can be used suitably. Needless to say, the liquid impervious resin film 11 does not include a liquid impervious resin film including a nonwoven fabric as a base material to enhance waterproofness.

It is desirable that the liquid impervious resin film 11 extends within the same range as or a wider range than the absorber 56 in the front-back direction LD and the width direction WD. However, for example, when another water blocking means is present, an end portion of the absorber 56 does not have to be covered in the front-back direction LD and the width direction WD as necessary. On an internal surface of the liquid impervious resin film 11, an indicator that is colored or decolored by a liquid component of excrement can be disposed. As the indicator, a known indicator can be used without particular limitation. For example, the indicator can be formed by a sheet-like member containing a coloring agent that exhibits a color reaction by contact with water in excrement and/or a coloring agent that detects the pH in water to exhibit a color reaction, an ink or an adhesive containing a chemical agent that exhibits a discoloration reaction due to a reaction with a liquid in excrement, a reaction that causes spread or discoloration of a coloring agent due to dissolution (dispersion) of the coloring agent by urine, or another visual change, or a chemical agent that exhibits a visual change by contact with water or a liquid in excrement (indicator reaction means). As the coloring agent that exhibits a color reaction by contact with water in excrement, a coloring agent containing a water-soluble and water-degradable dye or a leuco dye and a developer such as a phenolic compound, an acid substance, or an electron-accepting substance that develops a color of the leuco dye can be used.

(Exterior Nonwoven Fabric)

The exterior nonwoven fabric 12 covers the entire external surface side of the liquid impervious resin film 11 and imparts a cloth-like appearance to a product external surface. The exterior nonwoven fabric 12 is not particularly limited. Examples thereof as a material fiber include a synthetic fiber such as a polyolefin-based fiber including polyethylene and polypropylene, a polyester-based fiber, or a polyamide-based fiber, a regenerated fiber such as rayon or cupra, and a natural fiber such as cotton. Examples of a processing method include a spunlacing method, a spunbonding method, a thermal bond method, an air through method, and a needle punching method. However, a long-fiber nonwoven fabric such as a spunbonded nonwoven fabric, an SMS nonwoven fabric, or an SMMS nonwoven fabric is suitable from a viewpoint of achieving both texture and strength. A nonwoven fabric can be used in a single sheet or in a laminate formed of a plurality of sheets. In the latter case, the nonwoven fabrics are preferably bonded to each other with a hot melt adhesive or the like. In this case, the exterior nonwoven fabric 12 preferably has a fiber fineness of 1.0 to 6.0 dtex, a fiber basis weight of 10 to 45 g/m$^2$, and a thickness of 0.1 to 3.0 mm. However, the exterior nonwoven fabric 12 is not limited to those in these ranges.

When the exterior nonwoven fabric 12 has a cellulose nanofiber layer 15, a portion having the cellulose nanofiber layer 15 is inevitably hard, and an external surface of the absorbent article may have a hard texture. Therefore, it is preferable to make transmission of the hardness of the cellulose nanofiber layer 15 difficult to suppress deterioration of the texture of the external surface of the absorbent article by covering the cellulose nanofiber layer 15 with the relatively thick and firm exterior nonwoven fabric 12. In this case, the exterior nonwoven fabric preferably has a fiber fineness of 1.0 to 6.0 dtex, a fiber basis weight of 15 to 45 g/m$^2$, and a thickness of 0.5 to 3.0 mm. However, the exterior nonwoven fabric 12 having the cellulose nanofiber layer 15 is not limited to those in these ranges as long as making transmission of the hardness of the cellulose nanofiber layer 15 difficult to suppress deterioration of the texture of the external surface of the absorbent article.

(Rising Gather)

In order to block excrement that moves laterally on the top sheet 30 and to prevent so-called side leakage, rising gathers 60 rising on a skin side of a wearer are preferably disposed on both sides of an internal surface in the width direction WD. Of course, the rising gathers 60 can be omitted.

When the rising gather 60 is adopted, a structure thereof is not particularly limited, and any known structure can be adopted. The rising gather 60 in the illustrated example includes a gather sheet 62 substantially continuous in the width direction WD, and an elongated gather elastic member 63 fixed to the gather sheet 62 in a stretched state in the front-back direction LD. A water repellent nonwoven fabric can be used as the gather sheet 62, and a rubber thread or the like can be used as the gather elastic member 63. As illustrated in FIGS. 1 and 2, a plurality of elastic members may be disposed on each side, or one elastic member may be disposed on each side.

An internal surface of the gather sheet 62 has a bonding start point in the width direction WD on a side portion of the top sheet 30. A portion from the bonding start point to the outside in the width direction is bonded to an internal surface of each side flap portion SF, that is, in the illustrated example, bonded to a side portion of the liquid impervious resin film 11 and a side portion of the exterior nonwoven fabric 12 located in an outside thereof in the width direction with a hot melt adhesive or the like.

In a periphery of a leg, an inside of the bonding start point of the rising gather 60 in the width direction is fixed to the top sheet 30 at both end portions in a product front-back direction. However, a portion therebetween is a non-fixed free portion, and the free portion rises by a contraction force of the elastic member 63 and comes into close contact with a body surface.

(End Flap Portion and Side Flap Portion)

The tape-type disposable diaper in the illustrated example has a pair of end flap portions EF not including the absorber 56 and extending to a front side and a dorsal side of the absorber 56, and a pair of side flap portions SF not including the absorber 56 and extending to a lateral side more than both side edges of the absorber 56.

(Plane Gather)

To each side flap portion SF, a side elastic member 64 formed of an elongated elastic member such as a rubber thread is fixed in a stretched state in the front-back direction LD, and a periphery of a leg of each side flap portion SF is configured as a plane gather. The leg periphery elastic member 64 can be disposed between the gather sheet 62 and the liquid impervious resin film 11 outside the vicinity of the bonding start point in the width direction in the bonded portion of the gather sheet 62 as in the illustrated example, and can also be disposed between the liquid impervious resin film 11 and the exterior nonwoven fabric 12 in the side flap portion SF. A plurality of the leg periphery elastic members 64 may be disposed on each side as in the illustrated example, or only one leg periphery elastic member 64 may be disposed on each side.

(Connecting Tape)

In each side flap portion SF of the dorsal side portion B, a connecting tape 13 to be detachably connected to an external surface of the ventral side portion F is disposed. When the diaper 10 is worn, the connecting tapes 13 are turned along an external surface of the ventral side portion F from both sides of a waist, and the connecting portions 13A of the connecting tapes 13 are connected to appropriate positions of the external surface of the ventral side portion F.

The structure of the connecting tape 13 is not particularly limited. However, in the illustrated example, the connecting tape 13 includes: a tape attachment portion 13C fixed to the side flap portion SF; a sheet base material forming a tape main unit portion 13B protruding from the tape attachment portion 13C; and the ventral side connecting portion 13A disposed in a width direction intermediate portion of the tape main unit portion 13B in the sheet base material, and a tip side of the connecting portion 13A is a tab part.

As the connecting portion 13A, a hook material (hook member) of a mechanical fastener (hook and loop fastener) or a pressure-sensitive adhesive layer may be disposed. The hook material has many engaging projections on a connecting surface thereof. Examples of the shapes of the engaging projections include (A) tick shape, (B) J shape, (C) mushroom shape, (D) T shape, and (E) double J shape (a shape in which the J-shaped ones are connected to each other back to back), but any shape may be used.

As the sheet base material forming from the tape attachment portion 13C to the tape main unit portion 13B, a nonwoven fabric, a plastic film, a polylaminated nonwoven fabric, paper, or a composite material thereof can be used. However, a spunbonded nonwoven fabric, an air through nonwoven fabric, or a spunlaced nonwoven fabric having a fineness of 1.0 to 3.5 dtex, a basis weight of 20 to 100 g/m$^2$, and a thickness of 1 mm or less is preferable.

(Target Sheet)

A target sheet 20 having a target for facilitating connection is preferably disposed at a connecting location of the connecting tape 13 in the ventral side portion F. In a case where the connecting portion 13A is formed of a hook material, as the target sheet 20, it is possible to use one in which many loop threads making engaging projections of the hook material entangled therewith are disposed on an internal surface of a sheet base material formed of a plastic film or a nonwoven fabric. In a case of an adhesive material layer, it is possible to use one obtained by subjecting a surface of a sheet base material formed of a plastic film having a smooth surface with high adhesiveness to a peeling treatment. When the connecting location of the connecting tape 13 in the ventral side portion F is formed of a nonwoven fabric, for example, when the exterior nonwoven fabric 12 is disposed as in the illustrated embodiment, the target sheet 20 can be omitted, and the hook material can be entangled with fibers of the exterior nonwoven fabric 12 to be connected. In this case, the target sheet 20 as a mark may be disposed between the exterior nonwoven fabric 12 and the liquid impervious resin film 11.

(Cellulose Nanofiber)

The cellulose nanofibers refer to fine cellulose fibers obtained by defibrating pulp fibers, and generally refer to cellulose fibers containing cellulose fine fibers having an average fiber width of nano size (1 nm or more and 1000 nm or less). Cellulose nanofibers having an average fiber width (median diameter) of 100 nm or less are preferable, and cellulose nanofibers having 10 to 100 nm are particularly preferable. Within this range, the cellulose nanofiber layer has excellent contact efficiency with an odor and reduces an odor outside the absorbent article more effectively. However, the cellulose nanofibers are not limited to those in this range.

Cellulose fibers has a structure in which innumerable molecules of β glucose are mainly bonded to each other in a chain form with β-1,4 glycoside bonds. β-glucose has a —H group, a —OH group, and the like.

Here, a method for measuring the average fiber width of cellulose nanofibers is described.

First, 100 ml of an aqueous dispersion of cellulose nanofibers having a solid concentration of 0.01 to 0.1% by mass is filtered through a Teflon (registered trademark) membrane filter, and solvent substitution is performed once with 100 ml of ethanol and three times with 20 ml of t-butanol.

Next, the resulting product is lyophilized and coated with osmium to obtain a sample. This sample is observed with an electron microscope SEM image at a magnification of 5000, 10000, or 30000 (in this example, a magnification of 30000) depending on the width of a fiber forming the sample. Specifically, two diagonals are drawn on the observation image, and three straight lines passing the intersection of the diagonals are arbitrarily drawn. Furthermore, a total of 100 fiber rods intersecting the three straight lines are visually measured. Then, the median diameter of the measured values is taken as an average fiber width. Note that the average fiber width is not limited to the median diameter of measured values.

For example, a number average diameter or a mode diameter (most frequent diameter) may be taken as the average fiber diameter.

Examples of pulp fibers that can be used for manufacturing cellulose nanofibers include a chemical pulp such as a leaf bleached kraft pulp (LBKP) or a needle bleached kraft pulp (NBKP), a mechanical pulp such as a bleached thermomechanical pulp (BTMP), stone ground pulp (SGP), a pressed stone ground pulp (PGW), a refiner ground pulp (RGP), a chemiground pulp (CGP), a thermoground pulp (TGP), a ground pulp (GP), a thermomechanical pulp (TMP), a chemithermomechanical pulp (CTMP), or a refiner mechanical pulp (RMP), a waste paper pulp manufactured from brown waste paper, kraft envelope paper, magazine waste paper, newspaper waste paper, flyer waste paper, office waste paper, cardboard waste paper, high-quality white waste paper, Kent waste paper, simili waste paper, landowner certificate waste paper, or woody waste paper, and deinked pulp (DIP) obtained by deinking a waste paper pulp. These pulp fibers may be used singly or in combination of two or more types thereof as long as the effects of the present invention are not impaired. Furthermore, the pulp fiber may be subjected to a chemical treatment such as carboxymethylation.

Examples of a method for manufacturing cellulose nanofibers include mechanical methods such as a high-pressure homogenizer method, a microfluidizer method, a grinder grinding method, a bead mill freeze grinding method, and an ultrasonic defibrating method, but are not limited to these methods. In addition, nanofiber formation is promoted by combined use of a TEMPO oxidation treatment, a phosphoric acid esterification treatment, an acid treatment, and the like.

Characteristically, as illustrated in FIGS. 8 to 10, the cellulose nanofiber layer 15 can be disposed between the liquid impervious resin film 11 and the exterior nonwoven fabric 12. Note that a reference character H in FIGS. 8 to 10 represents an adhesive such as a hot melt adhesive for bonding the liquid impervious resin film 11 to the exterior nonwoven fabric 12. However, as described above, the liquid impervious resin film 11 may be bonded to the exterior nonwoven fabric 12 by welding or the like of a material. When such the cellulose nanofiber layer 15 is disposed between the liquid impervious resin film 11 and the exterior nonwoven fabric 12, an odor of excrement that has passed through the liquid impervious resin film 11 is adsorbed by the cellulose nanofiber layer 15. When the odor passes through the cellulose nanofiber layer 15 due to this adsorption, the concentration of the odor is reduced. For example, in a case where a wearer of a tape-type disposable diaper wears clothes outside the diaper, the remaining odor that has been once released to the outside of the diaper stays inside the clothes and is adsorbed again by the cellulose nanofiber layer 15 of the diaper. This further reduces the concentration of the odor diffused to the outside of the diaper.

In addition, since moisture is not blocked by the cellulose nanofiber layer 15, a stuffiness preventing property during wearing is unlikely to deteriorate. Furthermore, due to high hygroscopicity of the cellulose nanofibers, moisture is retained in the cellulose nanofiber layer 15, and a product external surface or an underwear does not easily impart a moist feel.

Note that the cellulose nanofiber layer 15 does not necessarily have to be disposed between the liquid impervious resin film 11 and the exterior nonwoven fabric 12, and only needs to be disposed in a region wrapping the absorber 56 from the outside when the diaper is formed into a discard form (substantially cylindrical form) as illustrated in FIG. 12. For example, in a case where the exterior nonwoven fabric 12 is not disposed, the cellulose nanofiber layer 15 may be disposed on an external surface of the liquid impervious resin film 11. Excrement exists in the absorber 56 or the liquid pervious top sheet 30. When the cellulose nanofiber layer 15 is disposed in the liquid impervious resin film 11 or the exterior nonwoven fabric 12 disposed on an external surface side of the absorber 56 or the liquid pervious top sheet 30, the liquid impervious resin film 11 or the exterior nonwoven fabric 12 surrounds excrement when a discard form (substantially cylindrical form) is formed. Therefore, diffusion of an odor to the outside can be reduced.

A tape-type disposable diaper that has been used is discarded as follows as an example. A diaper is removed from a wearer and rolled and wound from a ventral side edge to a dorsal side edge such that an internal surface of the diaper is an internal side of the winding. After the winding is completed, the connecting tape 13 extending outward in the width direction is fixed to the exterior nonwoven fabric 12 (external surface side of the diaper) such that the winding is not loosened. As a result, the diaper has a substantially cylindrical form as illustrated in FIG. 12(a). When the diaper is tightly wound without a gap (the number of windings is large), the substantially cylindrical form is relatively thin, and a side surface 91 of the substantially cylindrical form has a relatively small area. Meanwhile, when the diaper is wound with a gap (the number of windings is small), the substantially cylindrical form is relatively thick, and the side surface 91 of the substantially cylindrical form has a relatively large area. In addition, as an example of discarding a diaper, a diaper may be discarded as follows. A diaper is wound from a ventral side end to a dorsal side end so as to be rolled in a state where the diaper is unfolded. When the diaper is wound to the dorsal side end, the connecting tape 13 extending outward in the width direction is fixed to the exterior nonwoven fabric 12 (external surface side of the diaper) such that the winding is not loosened. However, how to discard a diaper varies depending on a guardian, and is not limited to the above method. Note that in a case where a tape 71 for disposal protrudes from both side portions of the dorsal side portion of the diaper or protrudes from a width direction intermediate portion of the dorsal side portion, a form is widely adopted in which the tape for disposal is fixed to an external surface of the diaper in a state where the diaper is rolled or folded such that an internal surface of the diaper is an internal side at the time of discard.

The number of windings depends on a guardian. Therefore, a range in which the cellulose nanofiber layer 15 is disposed is not particularly limited, but is preferably a range in which the liquid impervious resin film 11 overlaps with the exterior nonwoven fabric 12. In a case where the tape 71 for disposal and the connecting tape 13 are on the dorsal side of an external surface of the diaper, the length Y of the cellulose nanofiber layer 15 in the front-back direction LD is preferably a length from an edge of the diaper on the dorsal side to the center of the diaper. The length Y is preferably ½ of the maximum length L of the diaper, more preferably ⅓ thereof, and still more preferably ¼ thereof. When the cellulose nanofiber layer 15 is disposed in this range, the side surface 91 (that is, corresponding to the side surface 91 of the cylinder) when the diaper is formed into a substantially cylindrical form is surrounded by the cellulose nanofiber layer 15. In a case where the tape 71 for disposal and the connecting tape 13 are on the ventral side of an external surface of the diaper, the length Y of the cellulose nanofiber layer 15 in the front-back direction LD can be a length from an edge of the diaper on the ventral side to the center of the diaper.

Furthermore, the cellulose nanofiber layer 15 can be disposed in the entire range or a part of an external surface of the connecting tape 13. With this configuration, bottom surfaces 92 and 92 in the substantially cylindrical form are also completely surrounded by the cellulose nanofiber layer 15. Therefore, an odor is effectively reduced. The cellulose nanofiber layer 15 may be disposed in the entire range or a part of the side flap portion SF. However, the cellulose nanofiber layer 15 does not have to be disposed on the connecting tape 13 or the side flap portion SF depending on an application of the absorbent article without being limited to the above.

Note that an underpants-type disposable diaper is discarded as follows as an example. A diaper is removed from a wearer. The underpants-type disposable diaper is pre-folded such that a dorsal side and a ventral side fit to each other. The diaper is wound from the center of an external surface toward a ventral side edge so as to be rolled. After the winding is finished, the tape 71 for disposal disposed on a dorsal side external surface is extended toward a dorsal side edge, and is fixed to an external surface of the exterior nonwoven fabric 12 (external surface of the diaper) such that the winding is not loosened. As a result, the diaper has a substantially cylindrical form as illustrated in FIG. 12(b).

The present inventor has found that the cellulose nanofiber layer 15 has sufficient adhesiveness by itself, and has an effect of physically adsorbing an odor to reduce the odor. In a case where the cellulose nanofiber layer 15 is interposed between the liquid impervious resin film 11 and the exterior nonwoven fabric 12, the cellulose nanofiber layer 15 can come into contact with an odor in an atmosphere outside the disposable diaper. Therefore, the cellulose nanofiber layer 15 has high contact efficiency with an odor, and an odor outside the disposable diaper, particularly an odor inside a storage container when the disposable diaper is temporarily stored in the storage container can be reduced more effectively.

For example, a disposable diaper or the like is used in such a form that the disposable diaper or the like is rolled or folded such that an excrement adherence surface is an internal side after use to be formed into a discard form, put in a highly airtight storage container such as a sanitary box or a diaper storage container for temporary storage, and put in a garbage bag and discarded when the amount thereof stored in the container reaches a certain level. A strong odor of excrement is generated from the disposable diaper after use, causing discomfort to a user.

An external surface of the disposable diaper is covered with a dorsal side portion, and an odor generated from excrement adhering to an internal surface of the diaper or excrement absorbed by the absorber 56 is released to the outside through the dorsal side portion of the external surface. When the cellulose nanofiber layer 15 is disposed in the dorsal side portion, the cellulose nanofiber layer 15 is located in a main path of an odor in a discard form in which the diaper is rolled or folded, and therefore an odor reducing effect is exhibited more effectively. Furthermore, in a discard form in which the diaper is rolled or folded, the cellulose nanofiber layer 15 is located closer to the external surface. Therefore, an odor reducing effect is exhibited also to an odor existing outside the article, such as an odor in a storage container.

One of main components of an odor of excrement is methyl mercaptan ($CH_3SH$). The cellulose nanofiber layer 15 adsorbs methyl mercaptan to reduce the concentration of the odor of excrement. Adsorption is mainly caused by physical adsorption. Specifically, methyl mercaptan is adsorbed by the cellulose nanofiber layer 15 by Van der Waals force. Cellulose nanofibers generally have a fiber width of 4 nm or more and 1000 nm or less, a fiber length of 5 μm or more, a high aspect ratio (5 or more for cellulose nanofibers having a low aspect ratio, 1250 or more for cellulose nanofibers having a high aspect ratio), and a large specific surface area, and have an excellent physical adsorption property.

As illustrated in FIG. 8(b), the cellulose nanofiber layer 15 can be formed on an internal surface of the exterior nonwoven fabric 12. As illustrated in FIG. 9, a cellulose nanofiber film 15F can be disposed between the liquid impervious resin film 11 and the exterior nonwoven fabric 12. As illustrated in FIG. 10, a sheet 16 of a nonwoven fabric, paper, or the like having the cellulose nanofiber layer 15 formed thereon can be disposed between the liquid impervious resin film 11 and the exterior nonwoven fabric 12. However, as illustrated in FIG. 8(a), the cellulose nanofiber layer 15 is preferably formed on an external surface of the liquid impervious resin film 11. In addition, when the cellulose nanofiber layer 15 is applied onto the liquid impervious resin film 11 formed of a moisture pervious resin film, the cellulose nanofibers are formed into a film. Therefore, an odor reducing property of the liquid impervious resin film 11 and strength thereof are improved, and elongation is reduced advantageously. In particular, the liquid impervious resin film 11 formed of a moisture pervious resin film may be subjected to continuous decorative printing including many constituent units such as letters (size, brand name, manufacturer's name, pattern name, and the like) regularly repeated in the front-back direction LD and the width direction WD, patterns, or the like, or intermittent decorative printing for printing only one or both of the front and back of a product as in a product logo, a picture of a character, or a photograph. However, when such decorative printing is performed, the elongation of the liquid impervious resin film 11 is desirably small.

When the cellulose nanofiber layer 15 is applied onto the liquid impervious resin film 11 formed of a moisture pervious resin film, an odor reducing property of the liquid impervious resin film 11 and strength thereof are improved, but the liquid impervious resin film 11 is hard. Therefore, it is desirable that the basis weight of a base material of the liquid impervious resin film 11, that is, the basis weight of the moisture pervious resin film is reduced to, for example, about 10 to 12 g/m$^2$ to compensate for reduction in softness. Usually, reduction in the basis weight of the moisture pervious resin film to such a level may increase a possibility of generation of pinholes and may reduce a water blocking property. However, application of the cellulose nanofiber layer 15 onto the moisture pervious resin film can prevent such a reduction in water blocking property, and can exhibit an odor reducing effect.

In order to improve an odor reducing property, use of a larger amount of cellulose nanofibers is more preferable. However, when the amount is too large, a product is unnecessarily hard. Therefore, the application amount of the cellulose nanofiber layer 15 is preferably about 0.1 to 5.0 g/m$^2$. The application amount of the cellulose nanofiber layer 15 is more preferably about 0.5 to 3.0 g/m$^2$.

The cellulose nanofiber layer 15 can be disposed on the entire surface or a part of a range where the cellulose nanofiber layer 15 is disposed. In a case where the cellulose nanofiber layer 15 is disposed in a part of the range where the cellulose nanofiber layer 15 is disposed, the cellulose nanofiber layers 15 are preferably disposed at a large number of positions at intervals. For example, the cellulose nanofiber layers 15 can be disposed in a form of vertical stripes (see FIG. 11). In addition, the cellulose nanofiber layers 15 can be disposed in a form of horizontal stripes, in a form of diagonal stripes, or in a form of lattices. In this way, even when the cellulose nanofiber layers 15 are disposed at a large number of positions at intervals, the cellulose nanofiber layers 15 themselves have adhesiveness. Therefore, a part of the exterior nonwoven fabric 12 is unlikely to be curled, and is unlikely to be peeled off from the liquid impervious resin film 11.

Furthermore, the cellulose nanofiber layers 15 may be disposed between the liquid impervious resin film 11 and the exterior nonwoven fabric 12 at a plurality of positions at intervals, and may be attached directly to at least the liquid impervious resin film 11, the liquid impervious resin film 11 may be bonded to the exterior nonwoven fabric 12 at a portion not having the cellulose nanofiber layers 15 via a hot melt adhesive or the like, and a part or the whole of each of the cellulose nanofiber layers 15 does not have to be covered with the hot melt adhesive or the like. Considering adhesiveness of the cellulose nanofiber layer 15, contact efficiency thereof with an external odor, and texture of an external surface, it is preferable to attach the cellulose nanofiber layer 15 to an external surface of the liquid impervious resin film 11, and to cover an outside thereof with the exterior nonwoven fabric 12. Here, the exterior nonwoven fabric 12 is usually bonded to the liquid impervious resin film 11 via a hot melt adhesive or the like. However, covering the cellulose nanofiber layer 15 with a hot melt adhesive or the like is not desirable for improving contact efficiency between the cellulose nanofiber layer 15 and an odor. In contrast, as described above, when a structure is formed in which the cellulose nanofiber layers 15 are disposed at a plurality of positions at intervals, the liquid impervious resin film 11 is bonded to the exterior nonwoven fabric 12 at this interval portion, and a part or the whole of each of the cellulose nanofiber layers 15 is not covered with a hot melt adhesive or the like, it is possible to suppress a decrease in contact efficiency between each of the cellulose nanofiber layers 15 and an odor while the exterior nonwoven fabric 12 is bonded to the liquid impervious resin film 11, which is preferable.

In addition, the cellulose nanofiber layer 15 is hard. Therefore, when the cellulose nanofiber layer 15 is disposed continuously in a broad range, softness of a product may be impaired. In contrast, when the cellulose nanofiber layers 15 are disposed at intervals, it is possible to suppress a decrease in softness while the cellulose nanofiber layers 15 are disposed in a broad range. Meanwhile, cellulose nanofibers absorb an odor by physical adsorption. The cellulose nanofibers are fibrous, and therefore have a high aspect ratio and a relatively large specific surface area. Therefore, the cellulose nanofibers have a better physical adsorption property than general deodorant particles, and have a large odor reducing effect even if the cellulose nanofiber layers 15 are disposed at intervals. In addition, the use amount of the cellulose nanofibers can be reduced, and therefore cost effectiveness is also excellent.

In addition, the cellulose nanofiber layer 15 may be disposed only in a range where the cellulose nanofiber layer 15 overlaps with the absorber 56. A portion having the cellulose nanofiber layer 15 is inevitably hard. This is because the hardness of the cellulose nanofiber layer 15 is hidden by a cushioning property of the absorber 56 in a region where the cellulose nanofiber layer 15 overlaps with the absorber 56 on a skin side of a wearer.

The cellulose nanofiber layer 15 can be manufactured by a known method such as a method for forming cellulose nanofibers into a cellulose nanofiber dispersion, applying this cellulose nanofiber dispersion onto a target sheet such as the liquid impervious resin film 11, and drying the cellulose nanofiber dispersion to attach and form the cellulose nanofibers onto the target sheet. Note that when a liquid cellulose nanofiber is applied to a fiber sheet such as paper or a nonwoven fabric by a manufacturing method for applying a liquid cellulose nanofiber in this way, a part of the liquid cellulose nanofiber penetrates the sheet, but cellulose nanofibers concentrate on a surface. Therefore, the cellulose nanofiber layer 15 can be attached and formed onto the sheet. A solution in which the cellulose nanofibers are dispersed is not particularly limited, but examples thereof include water, a lower alcohol such as ethanol, and a volatile organic solvent such as acetone.

The cellulose nanofiber dispersion is obtained by dispersing cellulose nanofibers in water. The concentration (mass/volume) of the cellulose nanofiber dispersion is preferably 0.1 to 10%, more preferably 1.0 to 5.0%, and particularly preferably 1.5 to 3.0%.

The B-type viscosity (60 rpm, 20° C.) of the cellulose nanofiber dispersion is, for example, 300 cps or less, preferably 200 cps or less, and more preferably 50 cps or less. By suppressing the B-type viscosity of the cellulose nanofiber dispersion to a low level in this way, the cellulose nanofibers can be uniformly applied to a sheet surface, and the surface properties of the sheet are uniformly improved.

The cellulose nanofibers can be applied not only by spraying the cellulose nanofibers onto a target surface but also by using a transfer method with a letterpress method or the like.

The cellulose nanofibers are generally produced by decomposition of plants or biosynthesis using bacteria. The structures of the cellulose nanofibers are obtained by polymerizing glucose and are not considered to be harmful.

<Effect Confirmation Test>

Two types of effect confirmation tests of the cellulose nanofiber layer 15 were performed. The specifications of the absorber 56, the liquid impervious resin film 11, the exterior nonwoven fabric 12, and the cellulose nanofibers used in these effect confirmation tests are as follows.

Note that the absorber 56 is obtained by mixing pulp fibers and super absorbent polymer particles uniformly, and contains 180 g/m$^2$ of pulp fibers and 220 g/m$^2$ of super absorbent polymer particles.

As the super absorbent polymer particles, particles which had a water absorption capacity of 33 g/g, a water absorption rate of 35 seconds, and a gel strength of 3800 Pa, and in which a ratio of particles remaining on a standard sieve of 500 μm (JIS Z8801-1: 2006) was 18% by weight, and a ratio of particles remaining on a standard sieve of 180 μm (JIS Z8801-1: 2006) was 80% by weight when sieving using the standard sieve of 500 μm (shake for five minutes) was performed, and particles falling under the sieve using this sieving were sieved using the standard sieve of 180 μm (shake for five minutes), were used.

As the liquid impervious resin film 11, a moisture pervious polyethylene film having a basis weight of 18 g/m$^2$ was used. The moisture penetration of the liquid impervious resin film 11 (method of JIS Z 0208 temperature and humidity condition B (under conditions of temperature 40° C. and humidity 90%)) was 9000 g/m$^2$·24 h in effect confirmation test 1 and was 9000 g/m$^2$·24 h and 10000 g/m$^2$·24 h in effect confirmation test 2.

As the exterior nonwoven fabric 12, an air through nonwoven fabric with a basis weight of 20 g/m$^2$ with a composite fiber (fineness: 2.0 dtex) having a core-sheath structure of polyethylene (sheath) and polyethylene terephthalate (core) was used.

The cellulose nanofibers used in this test are NBKP 100% cellulose nanofibers. In addition, cellulose nanofibers having an average fiber width (median diameter) of 49 nm were used. These cellulose nanofibers were obtained by subjecting NBKP to a refiner treatment to be roughly defibrated, and then treating the roughly defibrated cellulose nanofibers four times using a high-pressure homogenizer to be defibrated. This average fiber width was measured by the above-described method for measuring the average fiber width of cellulose nanofibers.

<Effect Confirmation Test 1>

The following sample diaper was prepared, and the concentration of methyl mercaptan, which is a main component of an odor of excrement, was measured. A purpose of this test is to confirm how much the concentration of methyl mercaptan is reduced in a diaper having the cellulose nanofiber layer 15.

(Sample Diaper)

Samples of the diaper used in this test are as follows.

Sample 1 is a diaper in which the cellulose nanofiber layer 15 is disposed between the liquid impervious resin film 11 and the exterior nonwoven fabric 12, and a deodorant (sugar cane extract MSX-245 (manufactured by Mitsui Sugar Co., Ltd.)) is not applied.

Sample 2 is a diaper in which the cellulose nanofiber layer 15 is disposed on an internal surface of the liquid pervious top sheet 30, and the deodorant (MSX-245) is applied to an external surface of the exterior nonwoven fabric 12 (an external surface of the diaper).

Sample 3 is a diaper in which the cellulose nanofiber layer 15 is not disposed, and the deodorant (MSX-245) is applied to an external surface of the diaper.

Sample 4 is a diaper in which the cellulose nanofiber layer 15 is not disposed, and the deodorant (MSX-245) is not applied.

In Sample 1, 50 g of a cellulose nanofiber dispersion having a concentration of 0.1% was uniformly applied to the entire external surface of the liquid impervious resin film 11, and dried to prepare the liquid impervious resin film 11 having the 3.0 g/m$^2$ cellulose nanofiber layer 15. As the cellulose nanofibers, NBKP 100% cellulose nanofibers having an average fiber width (median diameter) of 49 nm were used.

In Sample 2, 50 g of a cellulose nanofiber dispersion having a concentration of 0.1% was uniformly applied to the entire internal surface of the liquid pervious top sheet 30, and dried to prepare the liquid pervious top sheet 30 containing 2.5 g of the deodorant (MSX-245) and the 3.0 g/m$^2$ cellulose nanofiber layer 15.

In Sample 3, 2.5 g of the deodorant (MSX-245) was dissolved in water to obtain 50 g of a solution. The solution was uniformly applied to the entire external surface of the liquid impervious resin film 11, and dried to prepare the liquid impervious resin film 11 containing the deodorant (MSX-245).

(Test Operation)

50 mL of methyl mercaptan having a concentration of 0.3% was injected into the center of the absorber 56 on an internal surface of the diaper. This diaper was put in a gas impervious bag, sealed, and allowed to stand. One hour after injection of the odorous liquid, the methyl mercaptan concentration in the bag was measured by a detector tube method. The detector tube method is a method for sucking 500 ml of gas to be tested with a detector tube and measuring the concentration (ppm) in the target gas. The detector tubes used were detector tubes methyl mercaptan No. 71 and 71H manufactured by Gastec Corporation.

(Results)

The methyl mercaptan concentration of the odorous liquid itself was 500 ppm per 500 mL of the gas. Table 1 illustrates measurement results with the detector tubes.

TABLE 1

| Unit | Application amount of cellulose nanofibers g/m$^2$ | Deodorant g | Concentration ppm | Odor reduction ratio % |
|---|---|---|---|---|
| Sample 1 | 3.0 | 0 | 200 | 42 |
| Sample 2 | 3.0 | 2.5 | 264 | 23 |
| Sample 3 | 0 | 2.5 | 249 | 27 |
| Sample 4 | 0 | 0 | 343 | 0 |

In Table 1, an odor reduction ratio of methyl mercaptan in sample n (n=1, 2, or 3) is determined by the following numerical formula.

[Numerical formula 1]

$$\text{Odor reduction ratio (\%)} = \frac{(\text{Concentration in sample 4 after elapse of one hour}) - (\text{Concentration in sample } n \text{ after elapse of one hour}) \times 100}{(\text{Concentration in sample 4 after elapse of one hour})}$$

In the numerical formula, the concentration in sample 4 after an elapse of one hour refers to the concentration of methyl mercaptan in the bag, measured one hour after sample 4 was put in the bag, sealed, and allowed to stand. The concentration in sample n after an elapse of one hour refers to the concentration of methyl mercaptan in the bag, measured one hour after sample n was put in the bag, sealed, and allowed to stand.

It is found that each of samples 1 to 3 has a lower concentration than sample 4, and has an odor reducing effect. When sample 1 is compared with sample 2, it is found that sample 1 has a higher odor reduction ratio. This is explained as follows. That is, this is because the odorous liquid dropped on the diaper is absorbed by the absorber 56, and sample 2 is a diaper in which the cellulose nanofiber layer 15 is disposed on an internal surface of the absorber 56 and cannot suppress diffusion of methyl mercaptan to an external surface side of the absorber 56.

When sample 1 is compared with sample 3, it is found that sample 1 has a higher odor reduction ratio. This indicates that the cellulose nanofiber layer 15 has a higher odor reduction ratio than the deodorant (MSX-245) under the conditions of this test. Therefore, it has been confirmed that sample 1 has a higher odor reduction ratio than samples 2 and 3.

<Effect Confirmation Test 2>

The following sample diaper was prepared, and the concentration of methyl mercaptan, which is a main component of an odor of excrement, was measured. A purpose of this test is to confirm how much the concentration of methyl mercaptan is reduced in a diaper having the cellulose nanofiber layer 15.

(Sample Diaper)

Samples of the diaper used in this test are as follows. There are nine samples of S1 to S9. As illustrated in Table 2, samples S1 to S6 each have a moisture penetration of 9000 g/m$^2$·24 h, and samples S7 to S9 each have a moisture penetration of 10000 g/m$^2$·24 h. The basis weight of the cellulose nanofiber layer 15 was adjusted between 0.1 and 1.5 g/m$^2$. The cellulose nanofiber layers 15 were disposed on the liquid impervious resin film 11 in a form of stripes with an application width of 5 mm and an application interval of 5 mm, and a hot melt adhesive 81 was applied only to a portion to which the cellulose nanofiber layer 15 was not applied. As the cellulose nanofibers, NBKP 100% cellulose nanofibers having an average fiber width (median diameter) of 49 nm were used.

(Test Operation)

Methyl mercaptan was dissolved in water such that the concentration (mass/volume) thereof was 0.5% to prepare an odorous liquid. 50 mL of this odorous liquid was injected into the center of the absorber 56 on an internal surface of the diaper. This diaper was put in a gas impervious bag, sealed, and allowed to stand. Zero hours, four hours, and 24 hours after injection of the odorous liquid, the concentration (ppm) of methyl mercaptan in the bag was measured by a detector tube method (JIS K 0804: 2014 detector tube gas measuring apparatus).

(Results)

Table 2 illustrates test results. In Table 2, the basis weight refers to the basis weight (g/m$^2$) when the cellulose nanofibers are applied to the liquid impervious resin film 11.

TABLE 2

| | | Sample S1 | Sample S2 | Sample S3 | Sample S4 | Sample S5 | Sample S6 | Sample S7 | Sample S8 | Sample S9 |
|---|---|---|---|---|---|---|---|---|---|---|
| Moisture penetration | | 9000 | 9000 | 9000 | 9000 | 9000 | 9000 | 10000 | 10000 | 10000 |
| Basis weight | | 0 | 0.1 | 0.3 | 0.5 | 1.0 | 1.5 | 0.5 | 0.5 | 0.5 |
| Immediately after injection | Concentration (ppm) | 1000 | 830 | 600 | 1000 | 800 | 900 | 400 | 800 | 500 |
| Four hours after injection | Concentration (ppm) | 600 | 350 | 300 | 400 | 230 | 200 | 200 | 250 | 300 |
| | Odor reduction ratio (%) | 40 | 58 | 50 | 60 | 71 | 78 | 50 | 69 | 40 |
| 24 hours after injection | Concentration (ppm) | 20 | 19 | 18 | 17 | 13 | 15 | 17 | 20 | 20 |
| | Odor reduction ratio (%) | 98 | 98 | 97 | 98 | 98 | 98 | 96 | 98 | 96 |

Table 2 illustrates the concentration (ppm) of methyl mercaptan measured immediately after injection of the odorous liquid (0 hours after the injection), four hours after the injection, or 24 hours after the injection, and an odor reduction ratio of methyl mercaptan (%) for samples S1 to S9. In Table 2, the odor reduction ratio (%) is determined by the following numerical formula.

[Numerical formula 2]

$$\text{Odor reduction ratio (\%)} = \frac{(\text{Concentration in sample } S1 \text{ immediately after injection}) - (\text{Concentration in sample } Sm \text{ } t \text{ hours after injection}) \times 100}{(\text{Concentration in sample } S1 \text{ immediately after injection})}$$

Here, in the numerical formula, the concentration in sample S1 immediately after the injection refers to the concentration of methyl mercaptan measured immediately after the odorous liquid is injected into the center of the absorber 56 for sample S1.

The concentration in sample Sm t hours after the injection refers to the concentration of methyl mercaptan measured after an elapse of t hours for sample Sm. m represents any one of 1 to 9, and t represents any one of 0, 4, and 24.

In Table 2, when the odor reduction ratio four hours after the injection was focused on, samples (S2 to S9) in which cellulose nanofibers are applied each tend to have a relatively higher odor reduction ratio than sample (S1) in which cellulose nanofibers are not applied. In particular, samples 4 to 6 each indicate a particularly high odor reduction ratio.

From this result, the application amount of cellulose nanofibers is preferably 0.1 $g/m^2$ or more, and more preferably 0.5 $g/m^2$ or more.

<Explanation of Terms in Specification>

The following terms in the specification have the following meanings unless otherwise specified in the specification.

"Front-back (longitudinal) direction LD" means a direction connecting a ventral side (front side) and a dorsal side (back side), and refers to "dorsoventral direction" in claims. "Width direction WD" means a direction orthogonal to the front-back direction (left-right direction).

"Unfolded state" means a flatly unfolded state without contraction or slackness.

"Stretch rate" means a value obtained when a natural length is 100%.

"Gel strength" is measured as follows. To 49.0 g of artificial urine (urea: 2% by weight, sodium chloride: 0.8% by weight, calcium chloride dihydrate: 0.03% by weight, magnesium sulfate heptahydrate: 0.08% by weight, deionized water: 97.09% by weight), 1.0 g of a super absorbent polymer is added, and the resulting mixture is stirred with a stirrer. The gel thus generated is left in a thermohygrostat at 40° C.×60% RH for three hours. Thereafter, the temperature is returned to room temperature, and gel strength is measured with a curdmeter (Curdmeter-MAX ME-500 manufactured by I. Techno Engineering Co., Ltd.).

"Basis weight" is measured as follows. A sample or a test piece is predried and then left in a test chamber or an apparatus in a standard state (test location is at a temperature of 23±1° C. and a relative humidity of 50±2%) so as to have a constant weight. Predrying refers to causing a sample or a test piece to have a constant weight in an environment of a temperature of 100° C. Note that fibers having an official moisture regain of 0.0% do not have to be predried. A sample of 100 mm×100 mm in size is cut out from a test piece having a constant weight using a template for sampling (100 mm×100 mm). The weight of the sample is measured. The weight is multiplied by 10 to calculate the weight per square meter to be used as a basis weight.

"Thickness" is automatically measured under conditions that a load is 0.098 $N/cm^2$ and a pressing area is 2 $cm^2$ using an automatic thickness meter (KES-G5 handy compression tester).

"Water absorption capacity" is measured in accordance with JIS K7223-1996 "Test method for water absorption capacity of super absorbent polymer".

"Water absorption rate" is "time to end point" when JIS K7224-1996 "Test method for water absorption rate of super absorbent polymer" is performed using 2 g of super absorbent polymer and 50 g of physiological saline.

In a case where environmental conditions in a test and a measurement are not described, the test and the measurement are performed in a test room or an apparatus in a standard state (test location is at a temperature of 23±1° C. and a relative humidity of 50±2%).

The size of each portion means a size not in a natural length state but in an unfolded state unless otherwise specified.

INDUSTRIAL APPLICABILITY

The present invention can be applied to general disposable diapers such as an underpants-type disposable diaper and a pad-type disposable diaper in addition to the tape-type disposable diaper as in the above example. Needless to say, the present invention can also be applied to another absorbent article such as a sanitary napkin.

REFERENCE SIGNS LIST

11 Liquid impervious resin film
12 Exterior nonwoven fabric
12A Bonded portion
13 Connecting tape
13A Connecting portion
13B Tape main unit portion
13C Tape attachment portion
15 Cellulose nanofiber layer
20 Target sheet
30 Top sheet
40 Intermediate sheet
56 Absorber
58 Wrapping sheet
60 Rising gather
62 Gather sheet
71 Tape for disposal
86, 88, 89 Elongated elastic member
91 Side surface
92 Bottom surface
B Dorsal side portion
F Ventral side portion
WD Width direction
LD Front-back direction

The invention claimed is:
1. An absorbent article comprising:
an absorber;
a liquid impervious resin film covering an outside of the absorber, and
an exterior nonwoven fabric covering an external surface of the liquid impervious resin film,
wherein a cellulose nanofiber layer is disposed between the liquid impervious resin film and the exterior nonwoven fabric at a plurality of positions at intervals in at least one of a front-back direction and a width direction, and is attached directly to at least the liquid impervious resin film,
wherein the liquid impervious resin film is bonded to the exterior nonwoven fabric via a hot melt adhesive at a portion not having the cellulose nanofiber layer,
wherein a whole of the cellulose nanofiber layer at each of the plurality of positions is not covered with the hot melt adhesive, and wherein the cellulose nanofiber layer is capable of contacting an odor in an atmosphere outside the absorbent article.

2. The absorbent article according to claim 1, comprising an exterior nonwoven fabric covering an external surface of the liquid impervious resin film, wherein
the cellulose nanofiber layer is interposed between the liquid impervious resin film and the exterior nonwoven fabric, and
the exterior nonwoven fabric has a fiber fineness of 1.0 to 6.0 dtex, a fiber basis weight of 15 to 45 g/m$^2$, and a thickness of 0.5 to 3.0 mm.

3. The absorbent article according to claim 2, comprising:
a ventral side portion located on a front side of a center in a front-back direction and a dorsal side portion located on a back side of the center in the front-back direction; and
a tape for disposal protruding from both side portions of the dorsal side portion or protruding from a width direction intermediate portion of the dorsal side portion, wherein
the cellulose nanofiber layer is disposed in the dorsal side portion, and the cellulose nanofiber layer is not disposed in the ventral side portion.

4. The absorbent article according to claim 2, wherein
the cellulose nanofiber layer is disposed only in a range where the cellulose nanofiber layer overlaps with the absorber.

5. The absorbent article according to claim 2, wherein
the cellulose nanofibers of the cellulose nanofiber layer have an average fiber width of 10 to 100 nm, and
the cellulose nanofiber layer includes 0.1 to 5.0 g/m$^2$ cellulose nanofibers.

6. The absorbent article according to claim 1, comprising:
a ventral side portion located on a front side of a center in a front-back direction and a dorsal side portion located on a back side of the center in the front-back direction; and
a tape for disposal protruding from both side portions of the dorsal side portion or protruding from a width direction intermediate portion of the dorsal side portion, wherein
the cellulose nanofiber layer is disposed in the dorsal side portion, and the cellulose nanofiber layer is not disposed in the ventral side portion.

7. The absorbent article according to claim 6, wherein
the cellulose nanofiber layer is disposed only in a range where the cellulose nanofiber layer overlaps with the absorber.

8. The absorbent article according to claim 6, wherein
the cellulose nanofibers of the cellulose nanofiber layer have an average fiber width of 10 to 100 nm, and
the cellulose nanofiber layer includes 0.1 to 5.0 g/m$^2$ cellulose nanofibers.

9. The absorbent article according to claim 1, wherein
the cellulose nanofiber layer is disposed only in a range where the cellulose nanofiber layer overlaps with the absorber.

10. The absorbent article according to claim 9, wherein
the cellulose nanofibers of the cellulose nanofiber layer have an average fiber width of 10 to 100 nm, and
the cellulose nanofiber layer includes 0.1 to 5.0 g/m$^2$ cellulose nanofibers.

11. The absorbent article according to claim 1, wherein
the cellulose nanofibers of the cellulose nanofiber layer have an average fiber width of 10 to 100 nm, and
the cellulose nanofiber layer includes 0.1 to 5.0 g/m$^2$ cellulose nanofibers.

* * * * *